United States Patent
Perovitch et al.

(10) Patent No.: US 10,758,479 B2
(45) Date of Patent: *Sep. 1, 2020

(54) GALENICAL FORM FOR THE ADMINISTRATION OF ACTIVE INGREDIENTS BY TRANSMUCOUS MEANS

(76) Inventors: Philippe Perovitch, Le Temple (FR); Marc Maury, Saint Medard en Jalles (FR)

(*) Notice: Subject to any disclaimer, the term of this patent is extended or adjusted under 35 U.S.C. 154(b) by 1473 days.

This patent is subject to a terminal disclaimer.

(21) Appl. No.: 12/441,762

(22) PCT Filed: Sep. 21, 2007

(86) PCT No.: PCT/FR2007/051993
§ 371 (c)(1),
(2), (4) Date: Mar. 18, 2009

(87) PCT Pub. No.: WO2008/035020
PCT Pub. Date: Mar. 27, 2008

(65) Prior Publication Data
US 2010/0022496 A1    Jan. 28, 2010

(30) Foreign Application Priority Data
Sep. 22, 2006 (FR) ...................... 06 53899

(51) Int. Cl.
*A61K 9/00* (2006.01)
*A61K 47/10* (2017.01)

(52) U.S. Cl.
CPC .............. *A61K 9/006* (2013.01); *A61K 47/10* (2013.01)

(58) Field of Classification Search
CPC combination set(s) only.
See application file for complete search history.

(56) References Cited

U.S. PATENT DOCUMENTS

| 3,001,403 | A | * | 9/1961 | Edwards | 435/307.1 |
|---|---|---|---|---|---|
| 5,629,022 | A | * | 5/1997 | Perovitch et al. | 424/489 |
| 5,683,721 | A | * | 11/1997 | Perovitch et al. | 424/489 |
| 8,722,744 | B2 | * | 5/2014 | Perovitch | 514/629 |
| 8,889,663 | B2 | * | 11/2014 | Perovitch | A61K 9/006 514/210.02 |
| 2002/0086878 | A1 | * | 7/2002 | Dobrozsi | 514/310 |
| 2002/0147201 | A1 | * | 10/2002 | Chen et al. | 514/252.15 |

FOREIGN PATENT DOCUMENTS

| GB | 2 392 093 | 2/2004 |
|---|---|---|
| WO | 00/41692 | 7/2000 |
| WO | 01/15666 | 3/2001 |

OTHER PUBLICATIONS

Terry White Chemists Amiodarone Tablets, pp. 1-14, available at www.medicines.org.au/files/twpamiod.pdf (2008).*
Latini et al, "Myocardial Disposition of Amiodarone in the Dog, Journal of Pharmacology and Experimental Therapeutics," vol. 224, No. 3, pp. 603-608 (1983).*
Perry et al, "TABLE 2-110 Ethyl Alcohol (C2H5OH)," Perry's Chemical Engineers' Handbook, 7th Ed., p. 2-112 (1 page) (1997).*
International Search Report dated Dec. 15, 2008, from corresponding PCT application.

* cited by examiner

*Primary Examiner* — Dennis J Parad
(74) *Attorney, Agent, or Firm* — Nixon & Vanderhye

(57) ABSTRACT

A galenical form for the administration transmucously of at least one active ingredient, characterized in that the active ingredient is in a stable and complete dissolved state in a hydroalcoholic solution that includes at least 20% by mass of alcohol so as to allow rapid absorption of the active ingredient through the mucous membranes of the buccal cavity and/or the oropharynx. Uses of the galenical form are also disclosed.

21 Claims, No Drawings

GALENICAL FORM FOR THE ADMINISTRATION OF ACTIVE INGREDIENTS BY TRANSMUCOUS MEANS

This invention relates to a galenical form for the instantaneous systemic administration by transmucous means of at least one active ingredient. The invention also relates to its uses.

Currently, there are a large number of pharmaceutical active ingredients that are designed to be self-administered by the patient himself.

This self-administration is generally carried out via the digestive tract.

However, when they are introduced into the alimentary canal and the stomach, the active ingredients undergo the so-called first digestive pass effect, alterations and losses related to the stomach environment or to variations of intestinal physiologies. They are then subjected to a so-called "first hepatic pass" effect, which brings about their metabolization and/or their more or less intense degradation, with composition of numerous metabolites, for the most part inactive or toxic.

The dose of truly bioavailable active ingredients is therefore extremely small: only one very residual part of the administered quantity remains valid to produce the pharmacologically expected effect.

Thus, by way of example, administered via the digestive tract, certain hormones are destroyed at more than 80%. Other substances such as Sumatriptan have a residual bioavailability that is reduced to less than 14% of the administered dose. It is also possible to cite analgesic opioids that have a bioavailability that varies between 10 and 40%.

In addition, these active ingredients generally have very short half-lives, less than the time it takes to reach plasmatic peaks.

It is also known that the beginning of the therapeutic effectiveness for the patient takes place at the earliest 45 minutes after intake, corresponding to the length of time for digestive absorption, metabolization and vascular diffusion, then tissue and optionally intracellular diffusion.

Actually, there are two major problems.

The first problem is that it is necessary to administer an adequate dose to the patient, taking into consideration the dilution and the dispersion in the organism, so that the significantly active part that reaches the affected zone is effective.

The second is the latency period due to the metabolization and the diffusion in the organism before the molecule acts and the patient feels its benefits.

Another administrative path, the per/sublingual path, which makes it possible to administer medications by passively passing through sublingual, jugal, gingival, lingual, palatine or pharyngeal mucous membranes, then passage into the sublingual veins and distribution to the general circulatory system, thus short-circuiting the digestive passage and the hepatic metabolism, is known.

Nevertheless, the existing sublingual formulations are not satisfactory, in particular because of the fact that most of the medications are unstable and consist of molecules that are by nature insoluble in biological liquids such as saliva. They are often complex, and a large portion of the molecules generally remains in crystalline form, thus making absorption, and therefore passage into the general circulatory system, impossible.

A need therefore persists for a galenical formulation that makes it possible to administer an immediately bioavailable quantity of active ingredient so as to be able to treat painful symptoms or incapacitating problems very promptly and effectively.

This is the purpose of this invention in proposing a galenical form for the administration by transmucous means of at least one active ingredient, whereby said active ingredient is in a stable and complete dissolved state in a hydroalcoholic solution that comprises at least 20% by mass of alcohol so as to allow rapid absorption of said active ingredient through the mucous membranes of the buccal cavity and/or the oropharynx.

Transmucous means is defined as any passive passing-through of a lipophilic or amphiphilic molecule through the lingual, sublingual, gingival, palatine, jugal mucous membranes or any other mucous membranes that constitute the buccal cavity and the oropharynx.

The stable and complete dissolved state is defined as a dissolved state that restores the active ingredient to the molecular and weakly ionized state in its dissolved medium, dissolved state that precludes any possibility of an inopportune recrystallization.

The active ingredients that are able to be formulated according to the invention are soluble molecules in hydroalcoholic mixtures. They are preferably lipophilic or amphiphilic in nature and of low molecular weight, less than 10,000 Da.

Preferably, the galenical form according to the invention comes in the form of a hydroalcoholic solution that comprises between 20 and 95% alcohol by mass and a water content of between 5 and 80%. The passage in the systemic circulation of the active ingredient(s) formulated according to the invention is therefore carried out in hydroalcoholic solution with the variable degree of alcohol, preferably between 20 and 95°.

According to a major characteristic of the invention, the alcohol, present at least 20% by mass, does not play only the role of solvent, but also that of promoter of an accelerated per-mucous absorption, whose speed increases based on the rise of the degree of alcohol that is used.

According to a preferred embodiment of the invention, the hydroalcoholic solution is produced based on water and ethanol.

According to another embodiment, the hydroalcoholic solution is produced with a base of water and isopropyl alcohol.

The hydroalcoholic solution according to the invention can also comprise one or more adjuvants for dissolution of the active ingredient(s), such as a polymer of the PEG (polyethylene glycol) type with low molecular weight, isopropyl alcohol, a surfactant such as Cremophor, or a polysorbate, and/or alcohol-oil mixtures. It can also contain an aroma or a sweetener for sweetening the taste sensation, but only if this proves necessary because any addition of vehicle(s) reduces the ratio of the absorbed dose at the same time that it reduces the per-mucous absorption speed of the active ingredient(s) that is/are being considered.

According to a particular embodiment, when the active ingredients to be administered contain a carbonyl acid group, the galenical form according to the invention can also comprise a pH-correcting agent and/or a sequestering agent. Actually, the active ingredients that contain a carbonyl acid group can react with the primary alcohols and the secondary alcohols for forming an ester. This reaction leads to the reduction in the content of active ingredient and to the appearance of impurities, which is incompatible with the preparation of a medication. The addition of at least one pH-correcting agent limits the H+ acid ion concentration that induces the esterification reaction, and the addition of at least one sequestering agent limits the concentration of metal ions that catalyze this reaction, which makes it possible to inhibit the formation of esters from the active ingredients that contain carbonyl ions.

Preferably, the pH-correcting agent is selected from among sodium carbonates and sodium bicarbonates, monosodium or disodium phosphates, triethanolamine, soda (NaOH) and potash (KOH). The sequestering agent is selected from among ethylene-diamine-tetraacetic acid (EDTA), calcium disodium ethylene diamine tetra-acetate (E385), glucono delta-lactone (E575), sodium gluconate (E576), potassium gluconate (E577) and sodium tripolyphosphate.

The galenical form according to the invention allows active ingredients to passively pass through the mucous membranes of the oropharynx in a length of time of less than 20 seconds after administration. This very rapid absorption period makes it possible to prevent any stagnation of the solution and of the active ingredient(s) in the buccal atmosphere as well as their inopportune mixing with saliva that can alter them, which would introduce a break in the continuity and the stability of the dissolution of the active ingredient(s). This short length of time also makes it possible to prevent any reflex swallowing of the solution and of the active ingredient(s) that it contains.

The transmucous passage of an active ingredient shown in the dissolved state according to the invention from the side of the external epithelial membrane, consisting of phospholipidic structures that passively absorb the lipophilic molecules by elective affinity, is based on an osmotic demand to the other side of said membrane, in which the concentration of dissolved active ingredient and that of the alcoholic solution being considered participate together. The osmotic demand is all the more enduring and powerful since the lipophilic molecule in the dissolved state has a low molecular weight and since the degree of alcohol that is used as an absorption promoter is high.

The mucous membranes of the mouth and the oropharynx have a very dense, quasi-spongy network of microvessels, so that the molecules, both of alcoholic solvent and dissolved active ingredient, which pass through the lipophilic pores of the epithelial membrane, are instantaneously captured by the blood micro-circulation and collected toward the sublingual veins. This phenomenon is accentuated by the presence of alcohol that causes a vasodilatation and an increase of the local microvascular flow rate of the mucous membranes.

Because of this locally elevated circulatory flow rate, increased by alcohol, there is therefore never equilibrium on either side of the membrane: the concentration in the mouth remains higher until the mechanism is exhausted when there are no more molecules to be absorbed.

Thus, the entirety of the alcohol and the active ingredient that is found dissolved therein according to the invention passes through the mucous membrane.

The use of the galenical form according to the invention makes it possible to administer an active ingredient dose that is immediately absorbed as soon as it is deposited and upon contact with the mucous membrane to be distributed instantaneously to the entire organism vascularly, without any delay for its pharmacological action and without undergoing the major effects of digestive and hepatic passages.

The hydroalcoholic solution with an alcohol content of at least 20% by mass according to the invention also has the advantage of solubilizing the active ingredients even if they are slightly soluble and of protecting the pharmaceutical formulation in relation to a microbiological contamination without having to introduce (an) antimicrobial preservation agent(s).

It allows the instantaneous systemic administration with reduced and useful doses of pharmacological agents, such as, for example, hormones, anti-hormones, and any active substances on the endocrine glands, cholesterol-lowering agents, anti-infective agents, anti-virals, anti-parasitics, vascular platelet inhibitors, molecules that treat menopause, andropause or sterility, instant contraceptives, analgesic agents, anti-inflammatory agents, anti-cancer substances, immunosuppressors, anti-migraine agents, anti-emetic agents, anti-diarrhea agents, anti-spasmodic agents, anti-allergy agents, anti-arrhythmic agents, erectogenic agents, anxiolytic agents, anti-diabetic agents, anti-hypertensives, anti-asthmatic agents, anti-parkinsonian agents and/or anti-histamine agents.

In particular, the galenical form according to the invention can be used for the production of a medication that is intended for the treatment and/or the prevention of migraine attacks, diarrhea syndromes, allergy attacks, vomiting, nauseated symptomatology, supra-ventricular and ventricular arrhythmia, Raynaud's Syndrome, erectile dysfunction, depression, panic disorders, obsessive-compulsive disorders (OCD), anxieties of the social phobia type, problems sleeping or waking up, diabetes, pulmonary diseases and asthma attacks, cyclic hormonal insufficiencies and dysmenorrhea, incapacitating, painful inflammatory attacks, Parkinson's disease or neuro-degenerative diseases.

Advantageously, this invention offers a great simplicity of production and a very good galenical stability: the specific regulation for each molecule of the water/alcohol solution ensures the solubilization of the active ingredient while eliminating most of the containers used in the conventional pharmaceutical forms and the traditional sublingual forms. It therefore makes it possible both to reduce the production costs and to reduce the risks of intolerance and the possible interactions between active ingredient(s) and vehicles.

Notably, the action times are very short, in particular compared to the slowness of absorption of medications by the digestive tract. The almost-instantaneous pharmacological release makes it possible for a patient to administer to himself a product for an effect that is almost equivalent to the effectiveness of a flash intravenous injection into the circulatory system.

In addition, since the active ingredient does not encounter any major obstacle to its assimilation and its instantaneous distribution into the organism, the basic administered dose is very low, very close to the useful dose for exerting the required pharmacological activity. This dose is preferably less than 300 mg of active ingredient.

Furthermore, whereby the oropharyngeal mucous membrane has an extremely large total adsorption surface area, scaled down by its nature of folded, villous tissue, the administration of the galenical form according to the invention is free of any risk of ill-timed swallowing or swallowing the wrong way. Actually, it allows an extremely fast permucous passage that prevents any salivary dissolving or swallowing of the active ingredients that are administered, with the advantage of not destabilizing the mucous membranes, with surfactant derivatives, for example, as is the case of the existing formulations.

Likewise, the effects of alcohol are insignificant. By way of example, 2 to 4 ml of ethanol at 40° C. would only produce a blood alcohol level of less than 8 or 16 mg per liter of blood, or, for example, 31.25 to 62.5 times below the legal French tolerances of 0.5 g of alcohol per liter of blood.

According to one aspect of the invention, the galenical form requires a specific industrial conditioning so as to prevent the degradation of the active ingredient(s) in contact with the air.

One particular embodiment consists in using an opaque, flexible, metalloplastic packaging that is filled under nitrogen atmosphere for the protection of the stability of the composition and the impermeability to oxygen and to radiation. This conditioning ensures the stability over time of the active ingredients that are dissolved in hydroalcoholic solution according to the invention.

For the comfort of use by the patient, for an easy transport, it is preferably possible to resort to "stick" passages in the form of specific single-dose or multi-dose airtight cases of a maximum capacity of 5 ml, which is the administration volume. Still more preferably, the galenical form according to the invention is conditioned in single-dose sticks of 0.25 to 5 ml, able to provide a suitable dose of active ingredient.

Advantageously, this conditioning is easy to transport and makes possible an easy use of the galenical form at any moment of the day.

Other characteristics and advantages will emerge from the following examples of the invention.

I. Example of Application to SUMATRIPTAN

Sumatriptan is the major anti-migraine agent and market reference. However, this molecule from the family of serotonin agonists, when it is administered enterally, has a period of action of about two hours, interminable relative to the waiting of any patient in pain, and an inadequate bioavailability.

It is possible to use the galenical form according to the invention for the administration of Sumatriptan. Such an administration makes it possible to produce effectiveness on the cerebral level in a period of several minutes only for a dosage of between, for example, 5 and 10 mg of basic Sumatriptan.

It is possible to cite two Sumatriptan example formulations according to the invention.

1—Example Formulation: 1 ml per 5 mg of Sumatriptan:

| | |
|---|---|
| Distilled water: | 0.65 ml |
| Ethanol, absolute alcohol: | 0.35 ml |
| Basic Sumatriptan: | 5.0 mg |
| Sweetener, sodium saccharinate and/or aroma, sufficient quantity | 0.3 mg |

2—Example Formulation: 2 ml per 10 mg of Sumatriptan:

| | |
|---|---|
| Distilled water: | 1.30 ml |
| Ethanol, absolute alcohol: | 0.70 ml |
| Basic Sumatriptan: | 10.0 mg |
| Sweetener, sodium saccharinate and/or aroma, sufficient quantity | 0.5 mg |

3—Example Formulation: 0.75 ml per 6 mg of Sumatriptan:

| | |
|---|---|
| Distilled water: | 0.45 ml |
| Ethanol, absolute alcohol: | 0.30 ml |
| Basic Sumatriptan: | 6.0 mg |
| Sweetener, sodium saccharinate and/or aroma, sufficient quantity | 0.5 mg |

The formulations according to the invention show good stability over time. The table below presents results of stability studies at 3 months, conducted on the example formulation 3:

| | Standards | J = 0 | J = 3 Months |
|---|---|---|---|
| CHARACTERISTICS | | | |
| Appearance | Liquid | As Specified | As Specified |
| Color | Light Brown | As Specified | As Specified |
| Odor | Vanilla-Caramel | As Specified | As Specified |
| TESTS: | | | |
| Purity (HPLC) | | | |
| Impurity A | ≤0.60% | 0.10% | 0.12% |
| Impurity H | ≤0.30% | <0.10% | <0.10% |
| Unknown Impurities | ≤0.20% | <0.10% | <0.10% |
| Impurity D | ≤0.50% | ND | ND |
| Unknown Impurities | ≤0.20% | ND | ND |
| Dosage of Ethyl Alcohol (CPG) | 40.0% | 40.7% | 39.0% |
| DOSAGE OF ACTIVE INGREDIENT Sumatriptan Content (HPLC 2) | 5.70 to 6.30 mg/Dose | 5.87 | 5.93 |
| MICROBIAL CONTAMINATION | | | |
| Bacteria | ≤1000/ml | <10/ml | |
| Yeasts and Molds | ≤100/ml | <10/ml | |
| *Escherichia coli* | Absence in 1 g | Absence in 1 g | |

II. Example of Application to LOPERAMIDE

Loperamide is an anti-diarrheal, anti-spasmodic and synthetic digestive analgesic agent of opioid type.

This molecule is generally metered at 2 mg and comes in gel form or in the form of solution to be taken orally.

However, when it is administered by the digestive tract, the loperamide undergoes a first digestive passing that leaves available only 40% of the administered dose, and then it undergoes a significant hepatic metabolization. The plasmatic peak is reached only at the end of two hours, and the portion of the effectively bioavailable dose would not be greater than 0.25 mg in the 2 mg administered.

It is possible to use the galenical form according to the invention for the administration of loperamide. Such an administration makes it possible to offer an almost-immediate relief to the patient whose pain and diarrheal syndromes are significantly reduced.

It is possible to cite two example formulations of loperamide according to the invention.

1—Example Formulation: 0.5 ml per 0.25 mg of Loperamide:

| | |
|---|---|
| Distilled water: | 0.35 ml |
| Ethanol, absolute alcohol: | 0.15 ml |
| Basic loperamide: | 0.25 mg |
| Sweetener, sodium saccharinate and/or aroma, sufficient quantity | 0.20 mg |

2—Example Formulation: 1 ml per 0.50 mg of Loperamide:

| | |
|---|---|
| Distilled water: | 0.70 ml |
| Ethanol, absolute alcohol: | 0.30 ml |
| Basic loperamide: | 0.50 mg |
| Sweetener, sodium saccharinate: | 0.30 mg |
| and/or aroma, sufficient quantity | |

III. Example of Application to Antihistamine Anti-Allergic Agents: LORATADINE and CETIRIZINE The antihistamine anti-allergic agents are medications whose purpose is to improve the comfort of allergy patients. They act specifically on a molecule that plays a primary role in the mechanisms of inflammation and allergy: the histamine.

Among the commonly-used, non-sedative, antihistamine anti-allergic agents, it is possible to cite loratadine and cetirizine. However, for the administration of 10 mg of these molecules by the digestive tract, the plasmatic peaks are reached only at the end of one hour, which does not constitute a suitable treatment for the allergic attack.

It is possible to use the galenical form according to the invention for the administration of loratadine or cetirizine. Such an administration makes it possible to reduce effectively the intensity of attacks in a rather short time, less than 15 minutes, which corresponds to the vascular passage of the active ingredient and then to its peripheral distribution at the tissue level to block the histamine-dependent receptors.

In addition, whereby the allergic reaction is always accompanied by a local hypervascularization, the galenical form according to the invention allows an easy access of the active ingredients to the affected areas.

It is possible to cite three example formulations of cetirizine according to the invention, and three example formulations of loratadine according to the invention.

1—Example Formulation: 0.5 ml per 1 mg of Cetirizine:

| | |
|---|---|
| Distilled water: | 0.365 ml |
| Ethanol, absolute alcohol: | 0.135 ml |
| Basic cetirizine: | 1.0 mg |
| Sweetener, sodium saccharinate | 0.2 mg |
| and/or aroma, sufficient quantity | |

2—Example Formulation: 1 ml per 3 mg of Cetirizine:

| | |
|---|---|
| Distilled water: | 0.675 ml |
| Ethanol, absolute alcohol: | 0.325 ml |
| Basic cetirizine: | 3.0 mg |
| Sweetener, sodium saccharinate | 0.40 mg |
| and/or aroma, sufficient quantity | |

3—Example Formulation: 1 ml per 5 mg of Cetirizine:

| | |
|---|---|
| Distilled water: | 0.575 ml |
| Ethanol, absolute alcohol: | 0.425 ml |
| Basic cetirizine: | 5.0 mg |
| Sweetener, sodium saccharinate | 0.6 mg |
| and/or aroma, sufficient quantity | |

4—Example Formulation: 0.5 ml per 1 mg of Loratadine:

| | |
|---|---|
| Distilled water: | 0.365 ml |
| Ethanol, absolute alcohol: | 0.135 ml |
| Basic loratadine: | 1.0 mg |
| Sweetener, sodium saccharinate | 0.2 mg |
| and/or aroma, sufficient quantity | |

5—Example Formulation: 1 ml per 3 mg of Loratadine:

| | |
|---|---|
| Distilled water: | 0.675 ml |
| Ethanol, absolute alcohol: | 0.325 ml |
| Basic loratadine: | 3.0 mg |
| Sweetener, sodium saccharinate | 0.4 mg |
| and/or aroma, sufficient quantity | |

6—Example Formulation: 1.5 ml per 5 mg of Loratadine:

| | |
|---|---|
| Distilled water: | 1.075 ml |
| Ethanol, absolute alcohol: | 0.425 ml |
| Basic loratadine: | 5.0 mg |
| Sweetener, sodium saccharinate | 0.6 mg |
| and/or aroma, sufficient quantity. | |

IV. Example of Application to Anti-Emetic Agents: METOPIMAZINE and DOMPERIDONE

The anti-emetic agents, such as metopimazine or domperidone, are medications that are commonly used for treating vomiting attacks.

They are generally administered under dosages of between 10 and 15 mg, in the form of tablets, freeze-dried tablets, syrups, or in the form of solutions to be taken orally.

However, these forms of administration all have a therapeutic inadequacy, because the molecules are very often rejected by the same vomiting episodes that they have to treat, before having had any effect.

It is possible to use the galenical form according to the invention for the administration of metopimazine or domperidone. Such an administration prevents the problem of the active ingredient being rejected by vomiting and allows an almost immediate therapeutic effect.

It is possible to cite an example formulation of metopimazine according to the invention, and an example formulation of domperidone according to the invention.

1—Example Formulation: 1 ml per 2 mg of Metopimazine:

| | |
|---|---|
| Distilled water: | 0.675 ml |
| Ethanol, absolute alcohol: | 0.325 ml |
| Basic metopimazine: | 2.0 mg |
| Sweetener, sodium saccharinate | 0.2 mg |
| and/or aroma, sufficient quantity | |

2—Example Formulation: 1 ml per 2 mg of Domperidone:

| | |
|---|---|
| Distilled water: | 0.550 ml |
| Ethanol, absolute alcohol: | 0.450 ml |
| Basic domperidone: | 2.0 mg |
| Sweetener, sodium saccharinate | 0.20 mg |
| and/or aroma, sufficient quantity | |

V. Example of Application to Anti-Nausea Agents: DIMENHYDRINATE and DIPHENHYDRAMINE Among the anti-nausea agents that are available on the market, in particular dimenhydrinate and diphenhydramine are known.

These molecules that are administered by the digestive tract have a strong hepatic metabolization and a period of action that is delayed relative to the intake, with a poor dose/effectiveness yield.

It is possible to use the galenical form according to the invention for the administration of dimenhydrinate or diphenhydramine. Such an administration makes possible an immediate bioavailability of low active doses and a rapid relief of nauseous symptomatology.

It is possible to cite an example formulation of dimenhydrinate according to the invention, and an example formulation of diphenhydramine according to the invention.

1—Example Formulation: 1 ml per 5 mg of Dimenhydrinate:

| | |
|---|---|
| Distilled water: | 0.650 ml |
| Ethanol, absolute alcohol: | 0.350 ml |
| Basic dimenhydrinate: | 5.0 mg |
| Sweetener, sodium saccharinate and/or aroma, sufficient quantity | 0.3 mg |

2—Example Formulation: 1.5 ml per 8 mg of Diphenhydramine:

| | |
|---|---|
| Distilled water: | 0.900 ml |
| Ethanol, absolute alcohol: | 0.600 ml |
| Basic dimenhydrinate: | 8.0 mg |
| Sweetener, sodium saccharinate and/or aroma, sufficient quantity | 0.6 mg |

VI. Example of Application to Anti-Arrythmic Agents

Currently, there are two major anti-arrythmic agents, amiodarone and flecainide.

Amiodarone is known for treating and preventing supraventricular and ventricular arrythmias whether they are supraventricular tachycardias, auricular fibrillations, arrhythmic tachycardias of the Wolff Parkinson White syndrome, severe ventricular arrythmias or else ventricular tachycardias and ventricular fibrillations. Amiodarone is also indicated in cardiorespiratory resuscitation in the case of cardiac arrest related to a ventricular fibrillation that is resistant to external electric shocks.

This previous therapeutic application is effective but produces significant and incapacitating secondary effects, related to excess iodine that is ingested and then released to obtain therapeutic concentrations.

Actually, in order for the amiodarone to be bioavailable, it is necessary that the entire organism be saturated with it so that it will then release it continuously.

Emergency treatment is problematic because it is necessary to administer high doses, the pharmacological action is very slow, and the use is limited to administration in a hospital setting so as to be able to monitor the secondary effects that are related to intake.

It is possible to use the galenical form according to the invention for the administration of amiodarone. Such an administration makes it possible to provide an active dose that is immediately absorbed by the endocardium, tissue and organic zone of the heart, which preferably monopolizes amiodarone by the so-called endocytosis mechanism just upon sole contact with the amiodarone-carrying circulating blood for a limited quantity circulating in the vascular network.

The dose/effect ratio is very good and can allow facilitated and prompt treatment of attacks without hospitalization.

The invention therefore offers the possibility of administering lower doses that can be adjusted over time and that are adapted to the pathological statue or to the level of therapeutic response from each patient.

It is possible to cite an example formulation of amiodarone according to the invention.

Example Formulation: 2 ml per 25 mg of Amiodarone:

| | |
|---|---|
| Distilled water: | 1 ml |
| Ethanol, absolute alcohol: | 1 ml |
| Basic amiodarone: | 25.0 mg |
| Sweetener, sodium saccharinate and/or aroma, sufficient quantity | 0.6 mg |

VII. Example of Application to Hormones

All of the hormones that are administered by the digestive tract undergo degradations in the digestive tube and then a first-pass hepatic hypermetabolism that both degrades their stereochemical structures and produces metabolites that are capable of generating secondary effect. Their residual bioavailability is therefore often very low.

It is possible to use the galenical form according to the invention for the administration of hormones. Such an administration makes possible an issuance and an attachment without delay to tissue hormonal receptors for an effective pharmacological activity with a large reduction of secondary effects.

Among the various hormones that are used in hormone therapies, it is possible to cite DHEA (DeHydroEpi-Androsterone). This hormone is produced by the organism to be used as a precursor to estrogens and to androgens. Its production level greatly decreases with age.

When it is administered by the digestive tract, the DHEA undergoes a considerable hepatic metabolism that produces metabolites that generate secondary androgenic and even carcinogenic effects.

This invention makes possible an administration of the dose that is necessary to the DHEA to compensate for the hormonal deficit that is related to age, without running the risk of secondary effects. It is possible to cite an example formulation of DHEA according to the invention.

Example Formulation: 2 ml per 10 mg of DHEA:

| | |
|---|---|
| Distilled water: | 1.2 ml |
| Ethanol, absolute alcohol: | 0.8 ml |
| Basic Sumatriptan: | 10.0 mg |
| Sweetener, sodium saccharinate and/or aroma, sufficient quantity | 0.6 mg |

Among the known hormones, it is also possible to cite estradiol, estrogenic hormone, currently administered by the nasal, per-mucous path, with a reduced mean bioavailability, less than 25% of the administered dose.

It is possible to use the galenical form according to the invention, with rapid vascular and tissue distribution, for administering estradiol. Advantageously, such an administration makes it possible to compensate for the sometimes incapacitating problems that arise suddenly, related to periods of insufficient estrogen levels.

Example Formulation: 0.5 ml per 100 µg of Estradiol:

| | |
|---|---|
| Distilled water: | 0.3 ml |
| Ethanol, absolute alcohol: | 0.2 ml |
| Basic estradiol: | 100 µg |

| | |
|---|---|
| Sweetener, sodium saccharinate and/or aroma, sufficient quantity | 0.1 mg |

VIII. Example of Application to Analgesic Anti-Inflammatory Agents

Among the commonly used analgesic anti-inflammatory agents, in particular ibuprofene, ketoprofene and diclofenac are known.

These molecules, when they are administered by the digestive tract, have a period of action that is more than one and one-half hours.

It is possible to use the galenical form according to the invention for the administration of these analgesic anti-inflammatory agents. Such an administration makes it possible to very quickly relieve various pains, be they articular, traumatic, and even migraine-related.

It is possible to cite an example formulation of diclofenac according to the invention.

Example Formulation: 1 ml per 10 mg of Diclofenac:

| | |
|---|---|
| Distilled water: | 0.55 ml |
| Ethanol, absolute alcohol: | 0.45 ml |
| Basic diclofenac: | 10.0 mg |
| Sweetener, sodium saccharinate and/or aroma, sufficient quantity | 0.5 mg |

IX. Example of Application to Erectogenic Agents

Three products dominate the erectogenic agent market: sildenafil, vardenafil and tadalafil.

These molecules have a bioavailability by a lesser oral path because of a very significant first hepatic pass. The pharmacological effect and the plasmatic peak of these molecules call for a period of 30 to 120 minutes, which involves an anticipated intake relative to the time when the erectogenic effect is anticipated.

It is possible to use the galenical form according to the invention for the administration of these erectogenic agents. Such an administration makes possible an immediate bioavailability of the active ingredient and therefore a very quick erectogenic effect on the order of several minutes.

It is possible to cite two example formulations of sildenafil according to the invention, and two example formulations of tadalafil according to the invention.

1—Example Formulation: 1 ml per 10 mg of Sildenafil:

| | |
|---|---|
| Distilled water: | 0.55 ml |
| Ethanol, absolute alcohol: | 0.45 ml |
| Basic sildenafil: | 10.0 mg |
| Sweetener, sodium saccharinate and/or aroma, sufficient quantity | 0.5 mg |

2—Example Formulation: 1.5 ml per 20 mg of Sildenafil:

| | |
|---|---|
| Distilled water: | 0.825 ml |
| Ethanol, absolute alcohol: | 0.675 ml |
| Basic sildenafil: | 20.0 mg |
| Sweetener, sodium saccharinate and/or aroma, sufficient quantity | 0.6 mg |

3—Example Formulation: 0.5 ml per 2 mg of Tadalafil:

| | |
|---|---|
| Distilled water: | 0.375 ml |
| Ethanol, absolute alcohol: | 0.225 ml |
| Basic tadalafil: | 2.0 mg |
| Sweetener, sodium saccharinate and/or aroma, sufficient quantity | 0.2 mg |

4—Example Formulation: 1 ml per 5 mg of Tadalafil:

| | |
|---|---|
| Distilled water: | 0.55 ml |
| Ethanol, absolute alcohol: | 0.45 ml |
| Basic tadalafil: | 5.0 mg |
| Sweetener, sodium saccharinate and/or aroma, sufficient quantity | 0.4 mg |

X. Example of Application to Anti-Asthmatic Agents

The current treatments of asthma by aerosol therapies are effective for ensuring the maintenance of balanced median bronchodilatation, but in the case of a massive, fast-onset bronchospasm, they prove to be totally ineffective.

Actually, more than half of the anti-asthmatic agents, such as salbutamol, salmeterol, (R) levosalbutamol, etc., administered by inhaled aerosols, do not exceed the oropharyngeal crossing or are absorbed by the esophagus. In addition, in the case of an asthma attack, the inspiratory blockage and the peripheral level of the bronchospasm ensure that inhaled treatments fail. A sudden and massive asthma attack therefore requires emergency intervention and an injection of anti-asthmatic agents by subcutaneous means.

It is possible to use the galenical form according to the invention for the administration of anti-asthmatic agents. Such an administration makes it possible for the patient to be independent to face the emergency and to halt the attack on his own, by an easy and quick means that requires only a simple gesture.

The molecules that are administered according to the invention immediately reach the right heart to be immediately distributed via the pulmonary arteries to all of the bronchial tissues inducing the instantaneous end of the bronchospasm.

It is possible to cite two example formulations of the salbutamol according to the invention:

1—Example Formulation: 0.5 ml per 25 mg of Salbutamol:

| | |
|---|---|
| Distilled water: | 0.275 ml |
| Ethanol, absolute alcohol: | 0.225 ml |
| Basic salbutamol: | 0.25 mg |
| Sweetener, sodium saccharinate and/or aroma, sufficient quantity | 0.10 mg |
| Hydrochloric acid or sulfuric acid, sufficient quantity to adjust the pH between 2 and 5. | |

2—Example Formulation: 1 ml per 0.5 mg of Salbutamol:

| | |
|---|---|
| Distilled water: | 0.575 ml |
| Ethanol, absolute alcohol: | 0.425 ml |
| Basic salbutamol: | 0.50 mg |
| Sweetener, sodium saccharinate and/or aroma, sufficient quantity | 0.3 mg |
| Hydrochloric acid or sulfuric acid, sufficient quantity to adjust the pH between 2 and 5. | |

It is possible to cite two example formulations of (R) levosalbutamol according to the invention.

1—Example Formulation: 0.5 ml per 0.25 mg of (R) Levosalbutamol:

| | |
|---|---|
| Purified water: | sufficient quantity for 0.5 ml |
| Ethanol, absolute alcohol: | 0.15 ml |
| Basic (R) levosalbutamol: | 0.1 g |
| Hydrochloric acid, sufficient quantity to adjust the pH between 2 and 5. | |

2—Example Formulation: 0.5 ml per 0.5 mg of (R) Levosalbutamol:

| | |
|---|---|
| Purified water: | sufficient quantity for 0.5 ml |
| Ethanol, absolute alcohol: | 0.15 ml |
| (R) Levosalbutamol: | 0.5 mg |
| Sulfuric acid, sufficient quantity to adjust the pH between 2 and 5. | |
| Sufficient quantity of aroma. | |

XI. Example of Application to Anti-Parkinson Agents: APOMORPHINE and SELEGILINE

Parkinson's disease is a disease of the extrapyramidal nervous system that is characterized by the triad "trembling, rigidity, akinesia."

The treatment is generally the L-DOPA that is combined with a decarboxylase inhibitor. This treatment gives rise to pharmacological escapes called "on/off" effects. During these effects, the patient finds himself in a situation where his dyskinesia reappears with a significant loss of independence.

There is currently a means of disrupting these episodes by subcutaneous injection of apomorphine chlorohydrate with a period of action of between 2 and 10 minutes and a duration of action of between 45 and 90 minutes.

Orally, apomorphine is virtually totally metabolized by the liver, with a bioavailability of between 1 and 2% of the dose, whereby all of the metabolites are inactive.

It is possible to use the galenical form according to the invention for the administration of apomorphine. Such an administration makes it possible for the Parkinsonian patient to disrupt his "on/off" states, independently, in a period of action that is at least as short as the subcutaneous intake.

Furthermore, to fight against the symptoms of Parkinson's disease, there is also selegiline, used in monotherapy or in support of the L-DOPA therapy. This molecule, a dopamine agonist, has a very short and low absolute bioavailability when taken orally.

The use of the galenical form according to the invention for the administration of the selegiline makes possible an instantaneous absorption with an almost-immediate and complete pharmacological activity.

It is possible to cite two example formulations of the apomorphine according to the invention, and two example formulations of selegiline according to the invention.

1—Example Formulation: 0.5 ml per 3 mg of Apomorphine:

| | |
|---|---|
| Distilled water: | 0.275 ml |
| Ethanol, absolute alcohol: | 0.225 ml |
| Basic apomorphine: | 3.0 mg |
| Sweetener, sodium saccharinate and/or aroma, sufficient quantity | 0.2 mg |

2—Example Formulation: 1 ml per 5 mg of Apomorphine:

| | |
|---|---|
| Distilled water: | 0.550 ml |
| Ethanol, absolute alcohol: | 0.450 ml |
| Basic apomorphine: | 5.0 mg |
| Sodium bisulfite: | 0.5 mg |
| Sweetener, sodium saccharinate and/or aroma, sufficient quantity | 0.4 mg |

3—Example Formulation: 0.5 ml per 0.25 mg of Selegiline:

| | |
|---|---|
| Distilled water: | 0.275 ml |
| Ethanol, absolute alcohol: | 0.225 ml |
| Basic selegiline: | 0.25 mg |
| Sodium bisulfite: | 0.2 mg |
| Sweetener, sodium saccharinate and/or aroma, sufficient quantity | 0.2 mg |

4—Example Formulation: 0.5 ml per 0.5 mg of Selegiline:

| | |
|---|---|
| Distilled water: | 0.275 ml |
| Ethanol, absolute alcohol: | 0.225 ml |
| Basic selegiline: | 0.5 mg |
| Sodium bisulfite: | 0.4 mg |
| Sweetener, sodium saccharinate and/or aroma, sufficient quantity | 0.2 mg |

Of course, the invention obviously is not limited to the examples shown and described above, but on the contrary covers all of the variants.

The invention claimed is:

1. A galenical form for the administration by transmucous means of one active ingredient, said galenic form consisting of one active ingredient and a hydroalcoholic solution based on water and ethanol, said active ingredient being in a stable and complete dissolved state in said hydroalcoholic solution such that said active ingredient is in a molecular state in the hydroalcoholic solution, wherein said galenic form is in a liquid form, and said hydroalcohlic solution consists of at least 20% by mass of ethanol and 50%-73% by volume of water and 27%-50% by volume of ethanol so as to allow rapid absorption in less than 20 seconds of all of said active ingredient through the gingival and/or jugal mucous membranes of the buccal cavity, wherein the dose of said active ingredient is less than 300 mg and the volume of said hydroalcoholic solution is less than 5 ml.

2. The galenical form according to claim 1, wherein said active ingredient has a molecular weight that is less than 10,000 Da.

3. The galenical form according to claim 1, wherein it allows active ingredient to passively pass through the mucous membranes of the oropharynx in a time period of less than 20 seconds after administration.

4. The galenical form according to claim 1, wherein the active ingredient is selected from among the hormones, the anti-hormones, and any active agents on the endocrine glands, cholesterol-lowering agents, anti-infective agents, anti-viral agents, anti-parasitic agents, vascular platelet inhibitors, molecules that treat menopause, andropause or sterility, instant contraceptives, analgesic agents, anti-inflammatory agents, anti-cancer agents, immunosuppressors, anti-migraine agents, anti-emetic agents, anti-diarrhea agents, anti-spasmodic agents, anti-allergy agents, anti-arrythmic agents, erectogenic agents, anxiolytic agents, antidiabetic agents, anti-hypertensive agents, anti-asthmatic agents, anti-parkinsonian agents and/or antihistamine agents.

5. The galenical form according to claim 1, wherein said active ingredient is sumatriptan, and wherein said hydroalcoholic solution is selected from the group consisting of (i) a solution containing 65% by volume of water and 35% by volume of ethanol and (ii) a solution containing 60% by volume of water and 40% by volume of ethanol.

6. The galenical form according to claim 1, wherein said active ingredient is loperamide or levosalbutamol, and wherein said hydroalcoholic solution contains 70% by volume of water and 30% by volume of ethanol.

7. The galenical form according to claim 1, wherein said active ingredient is cetirizine, and wherein said hydroalcoholic solution is selected from the group consisting of (i) a solution containing 73% by volume of water and 27% by volume of ethanol, (ii) a solution containing 67.5% by volume of water and 32.5% by volume of ethanol, and (iii) a solution containing 57.5% by volume of water and 42.5% by volume of ethanol.

8. The galenical form according to claim 1, wherein said active ingredient is loratadine, and wherein said hydroalcoholic solution is selected from the group consisting of (i) a solution containing 73% by volume of water and 27% by volume of ethanol, (ii) a solution containing 67.5% by volume of water and 32.5% by volume of ethanol and (iii) a solution containing 71.67% by volume of water and 28.33% by volume of ethanol.

9. The galenical form according to claim 1, wherein said active ingredient is metopimazine, and wherein said hydroalcoholic solution contains 67.5% by volume of water and 32.5% by volume of ethanol.

10. The galenical form according to claim 1, wherein said active ingredient is selected from the group consisting of domperidone, diclofenac, sildenafil, tadalafil, salbutamol, apomorphine, and selegiline, and wherein said hydroalcoholic solution contains 55% by volume of water and 45% by volume of ethanol.

11. The galenical form according to claim 1, wherein said active ingredient is dimenhydrinate, and wherein said hydroalcoholic solution contains 65% by volume of water and 35% by volume of ethanol.

12. The galenical form according to claim 1, wherein said active ingredient is selected from the group consisting of diphenhydramine, DHEA, and estradiol, and wherein said hydroalcoholic solution contains 60% by volume of water and 40% by volume of ethanol.

13. The galenical form according to claim 1, wherein said active ingredient is amiodarone, and wherein said hydroalcoholic solution contains 50% by volume of water and 50% by volume of ethanol.

14. The galenical form according to claim 1, wherein said active ingredient is salbutamol, and wherein said hydroalcoholic solution contains 57.5% by volume of water and 42.5% by volume of ethanol.

15. The galenical form according to claim 1, wherein said active ingredient is selected from the group containing sumatriptan, loperamide, cetirizine, loratadine, metopimazine, domperidone, dimenhydrinate, diphenhydramine, amiodarone, DHEA, estradiol, diclofenac, sildenafil, tadalafil, salbutamol, levosalbutamol, apomorphine, selegiline.

16. The galenical form according to claim 1, wherein said active ingredient contains a carbonyl acid group.

17. A galenical form for the administration by transmucous means of one active ingredient, said galenic form consisting of one active ingredient, a hydroalcoholic solution based on water and ethanol and a pH-correcting agent, said active ingredient being in a stable and complete dissolved state in said hydroalcoholic solution such that said active ingredient is in a molecular state in the hydroalcoholic solution, wherein said galenic form is in a liquid form, and said hydroalcohlic solution consists of at least 20% by mass of ethanol and 50%-73% by volume of water and 27%-50% by volume of ethanol so as to allow rapid absorption in less than 20 seconds of all of said active ingredient through the gingival and/or jugal mucous membranes of the buccal cavity, wherein the dose of said active ingredient is less than 300 mg and the volume of said hydroalcoholic solution is less than 5 ml.

18. A method for the administration by transmucous means of one active ingredient, comprising administering a galenical form according to claim 1, said galenical form allowing rapid absorption of said active ingredient through the mucous membranes of the buccal cavity and/or the oropharynx.

19. The method according to claim 18, wherein the galenical form allows said active ingredient to passively pass through the mucous membranes of the oropharynx in a time period of less than 20 seconds after administration.

20. The method according to claim 18, wherein the galenical form is administered in a volume less than 5 ml.

21. The method according to claim 18, wherein said active ingredient is selected from the group consisting of hormones, anti-hormones, and any active agents on the endocrine glands, cholesterol-lowering agents, anti-infective agents, anti-viral agents, anti-parasitic agents, vascular platelet inhibitors, molecules that treat menopause, andropause or sterility, instant contraceptives, analgesic agents, anti-inflammatory agents, anti-cancer agents, immunosuppressors, anti-migraine agents, anti-emetic agents, anti-diarrhea agents, anti-spasmodic agents, anti-allergy agents, anti-arrythmic agents, erectogenic agents, anxiolytic agents, anti-diabetic agents, anti-hypertensive agents, anti-asthmatic agents, anti-parkinsonian agents, antihistamine agents and combinations thereof.

* * * * *